US011160569B2

(12) United States Patent
Razavi et al.

(10) Patent No.: US 11,160,569 B2
(45) Date of Patent: Nov. 2, 2021

(54) ESOPHAGEAL PROBES AND METHODS

(71) Applicants: Baylor College of Medicine, Houston, TX (US); Texas Heart Institute, Houston, TX (US)

(72) Inventors: Mehdi Razavi, Houston, TX (US); Robert Paisley, Houston, TX (US)

(73) Assignees: Texas Heart Institute; Baylor College of Medicine

( * ) Notice: Subject to any disclaimer, the term of this patent is extended or adjusted under 35 U.S.C. 154(b) by 685 days.

(21) Appl. No.: 15/760,473

(22) PCT Filed: Sep. 19, 2016

(86) PCT No.: PCT/US2016/052542
§ 371 (c)(1),
(2) Date: Mar. 15, 2018

(87) PCT Pub. No.: WO2017/049313
PCT Pub. Date: Mar. 23, 2017

(65) Prior Publication Data
US 2018/0317943 A1 Nov. 8, 2018

Related U.S. Application Data

(60) Provisional application No. 62/220,088, filed on Sep. 17, 2015.

(51) Int. Cl.
*A61B 18/04* (2006.01)
*A61B 17/22* (2006.01)
(Continued)

(52) U.S. Cl.
CPC .......... *A61B 17/22* (2013.01); *A61B 17/0218* (2013.01); *A61B 17/24* (2013.01);
(Continued)

(58) Field of Classification Search
CPC ...... A61B 18/1492; A61B 2018/00285; A61B 2018/00291; A61B 2018/00351;
(Continued)

(56) References Cited

U.S. PATENT DOCUMENTS 7,507,238 B2 * 3/2009 Edwards ................ A61B 18/12
128/898
2003/0195501 A1 10/2003 Sherman et al.
(Continued)

OTHER PUBLICATIONS

Translation of an Office action dated Jul. 28, 2020, in the corresponding Japanese application serial No. JP2018514880A, 6 pages.
(Continued)

*Primary Examiner* — Daniel W Fowler
(74) *Attorney, Agent, or Firm* — Jonathan Pierce; Pierre Campanac; Porter Hedges LLP (57) ABSTRACT

Methods for collapsing a tubular organ, such as the esophagus, involve inserting a device into the tubular organ, at least partially sealing off a section of the tubular organ, and drawing in the wall of the tubular organ by application of suction. The devices may be used to move the wall of the tubular organ away from an area undergoing treatment or therapy, such as to minimize damage to the tubular organ by application of radiofrequency energy or to limit temperature increase of the tubular organ.

16 Claims, 5 Drawing Sheets

(51) Int. Cl.
  *A61B 18/14* (2006.01)
  *A61B 17/02* (2006.01)
  *A61B 17/24* (2006.01)
  *A61B 17/30* (2006.01)
  *A61B 18/00* (2006.01)
  *A61B 90/00* (2016.01)
  *A61B 1/00* (2006.01)
  *A61B 1/32* (2006.01)

(52) U.S. Cl.
  CPC .......... *A61B 17/30* (2013.01); *A61B 18/1492* (2013.01); *A61B 1/00* (2013.01); *A61B 1/32* (2013.01); *A61B 2017/22054* (2013.01); *A61B 2017/22067* (2013.01); *A61B 2017/306* (2013.01); *A61B 2018/00285* (2013.01); *A61B 2018/00291* (2013.01); *A61B 2018/00351* (2013.01); *A61B 2018/00488* (2013.01); *A61B 2018/00702* (2013.01); *A61B 2018/00714* (2013.01); *A61B 2018/00791* (2013.01); *A61B 2018/00875* (2013.01); *A61B 2090/0427* (2016.02); *A61B 2090/064* (2016.02); *A61B 2090/08021* (2016.02)

(58) Field of Classification Search
  CPC .......... A61B 2018/00488; A61B 2018/00702; A61B 2018/00791; A61B 2018/00875; A61B 17/0218; A61B 17/22; A61B 17/24; A61B 17/30
  See application file for complete search history.

(56) References Cited

U.S. PATENT DOCUMENTS

| | | | |
|---|---|---|---|
| 2004/0199155 A1 | 10/2004 | Mollenauer | |
| 2006/0074410 A1* | 4/2006 | Malecki | A61B 18/1492 606/32 |
| 2006/0106375 A1* | 5/2006 | Werneth | A61B 18/1492 606/32 |
| 2008/0033415 A1 | 2/2008 | Rieker et al. | |
| 2008/0077126 A1* | 3/2008 | Rashidi | A61B 18/1492 606/34 |
| 2011/0082488 A1 | 4/2011 | Niazi | |
| 2013/0317390 A1* | 11/2013 | Levy | A61B 10/04 600/563 |
| 2014/0316406 A1* | 10/2014 | Willis | A61B 18/1492 606/41 |
| 2014/0336753 A1 | 11/2014 | Taylor et al. | |
| 2015/0157820 A1 | 6/2015 | Razavi et al. | |
| 2015/0216442 A1 | 8/2015 | Lavy et al. | |
| 2017/0360503 A1 | 12/2017 | Miller | |

OTHER PUBLICATIONS

Jacob S. Koruth et al., Mechanical Esophageal Displacement During Catheter Ablation for Atrial Fibrillation, Journal of Cardiovascular Electrophysiology, Feb. 2012, pp. 147-154, vol. 23. No. 2.

* cited by examiner

ESOPHAGEAL PROBES AND METHODS

CROSS-REFERENCE TO RELATED APPLICATIONS

This application claims the benefit and priority of U.S. provisional patent application Ser. No. 62/220,088, filed Sep. 17, 2015, entitled "Esophageal probe", the content of which is hereby incorporated by reference in its entirety.

FIELD OF THE INVENTION

The invention relates to devices and methods for collapsing a tubular organ, such as the esophagus. The tubular organ may be collapsed by inserting a device into the tubular organ, at least partially sealing off a section of the tubular organ, and moving the wall of the tubular organ by application of suction. This invention further relates to methods of using such device to move the wall of the tubular organ away from an area undergoing a treatment or therapy, such as to minimize damage to the tubular organ by application of radiofrequency energy or by increased temperature.

BACKGROUND OF THE INVENTION

Atrial fibrillation ablation involves delivery of radiofrequency (RF) energy to heart tissue. RF energy leads to thermal damage and ablation of the tissue. This is the primary means by which it creates its therapeutic effects. Because of the proximity of the heart's left atrium to the esophagus, ablation of tissue of the left atrium (especially tissue of the posterior wall of the left atrium or in the regions near the pulmonary veins) can lead to delivery of RF energy to the esophagus. Thermal damage and secondary lesions may extend to esophageal tissue. This is a potential and likely mechanism of atrioesophageal fistula (AEF), a rare but lethal complication of the procedure. Approximately 75% of patients who have AEF will die from the condition. There has been a steady increase in the body of literature suggesting that the most effective means of protecting a patient from AEF is by avoiding thermal damage in the regions close to the esophagus. What is clear to every practitioner of ablation (cardiac electrophysiologists) is that thermal damage in regions close to the esophagus is to be avoided. Unfortunately these areas are often the major triggers of atrial fibrillation in the first place. Thus avoiding ablation in the regions around the esophagus may in fact lead to lower success rates of the ablation procedure and lower rates of cure of atrial fibrillation.

A variety of techniques have attempted to thermally isolate the esophagus from the left atrium during the course of ablation. These include placement of a thermal probe in the form of a radioopaque or radiolucent catheter. The probe partially covers the overall outline of the esophagus in the portion that traverses along the posterior aspect of the left atrium. It will also sense temperature to alert an operator whether or not RF energy application is leading to increased local (intraluminal) esophageal temperatures. Such temperature increases have been theorized to trigger fistula formation. Other techniques include administration of esophageal contrast bath and irrigation of the esophagus using a cold saline solution so as to cool the esophagus during ablation and protect it from thermal damage. Given the relative infrequency of the use of these intervention techniques, it is difficult to assess what effect, if any, these intervention techniques have on the development of AEF.

Alternatively, it may be desirable to be able to displace the esophagus selectively so that in the course of ablation it can be moved away from the proximity of the ablation catheter. Nasogastric tubes with deflection catheters have been suggested to be effective. There are current technologies that rely on deflection of the esophagus using an endoscopic or nasogastric tube. These technologies, however, require use of a more expensive deflectable catheter and manipulation of the catheter so that the esophagus is in fact mobilized effectively. This can be quite cumbersome and may necessitate use of additional personnel. Given the large numbers of such procedures the economic impact of using mechanical deflection of the esophagus will likely be prohibitive. Further, the entire esophageal profile as it courses over the catheter is usually not known unless contrast is used, therefore leaving the risk that a portion of the esophagus remains too close to the region where RF energy is delivered. Furthermore, endoscopic deflection pushes the esophagus laterally within the chest cavity, i.e. closer to one chest wall than the opposite. A deflection catheter may poke, or excessively stretch, the esophagus, increasing the risk of perforating the esophagus, and possibly triggering fistula formation.

SUMMARY OF THE INVENTION

The invention relates to devices and methods for collapsing a tubular organ, such as the esophagus. The tubular organ may be collapsed by inserting a device into the tubular organ, at least partially sealing off a section of the tubular organ, and moving the wall of the tubular organ by application of suction. This invention further relates to methods of using such device to deform the wall of the tubular organ away from an area undergoing a treatment or therapy, such as to minimize damage to the tubular organ by application of radiofrequency energy or by increased temperature.

In general, a device for collapsing a tubular organ may be utilized on a variety of body structures, such as, for example, the esophagus. The device may generally include a tube which is inserted into a tubular organ proximal to an area to be affected by the device.

In one aspect of the invention, the device may include a tube portion having a proximal end and a distal end. The tube portion has an outer surface with at least one fenestration or other port through which suction or other means of drawing fluid or gas may be applied to the area surrounding the tube portion. The fenestration may be disposed between the proximal and distal end of the tube portion. In some embodiments, the tube portion may include a plurality of fenestrations or ports which may be utilized to apply suction or other means to different locations along the tube portion or, for example, to equalize the applied suction or other means along a larger area of the tube portion than with a single fenestration or port. The fenestrations or ports may be connected to an external source of suction or other means, such as through internal lumens formed into the tube portion or with internal conduits carried within a connecting conduit.

In another aspect of the invention, the device may further include at least one sealing feature to isolate a portion of a tubular organ to be collapsed by the device. In general, the sealing feature may form at least a partial seal against the wall of the tubular organ. The seal may be reversible, in the sense that the sealing feature may be expandable/contractible or otherwise changeable in state from a sealing to a non-sealing configuration. Sealing features may include, for example, deformable or compressible formations about the tube portion of the device. In some embodiments, the sealing feature may include a balloon or other feature that may be selectively expanded to contact the wall of the tubular organ or deflated/contracted to draw away from the wall, such as to aid in moving the device in the tubular organ without additional contact or friction with the wall. The balloon or other feature may also generally be connected to a fluid or gas source or withdrawing device, such as a suction line or pump, and the connection may generally be carried by lumen(s) or conduit(s)/tube(s) within the connection conduit and connected to an external source or device.

In some embodiments, the device may include at least two sealing features along the length of the tube portion, such that, for example, the fenestrations or ports (or groupings of them) lie between the two sealing features. The two sealing features may then, for example, seal off a particular length of the tubular organ at either end of the particular length to be deformed by the device. In other embodiments, three or more sealing features may be utilized to, for example, create multiple separate particular lengths to be deformed separately. Where balloons or other selectively expandable/contractible features are utilized, they may be individually controlled or controlled in groupings.

In a further aspect of the invention, the device may further include sensors or other features for aiding in locating the device within the tubular organ and/or for detecting a desired area of the tubular organ to be deformed by the device. In some embodiments, desired areas of the tubular organ may be determined by detected conditions in the area, such as temperature, pressure, electrical resistance/conductivity, and/or any other appropriate condition or combination thereof. For example, temperature may be detected to determine where a tubular organ may need to be acted on, such as, for example, to aid in protecting it from damage from a temperature increase in the vicinity. For further example, pressure or other indicators of contact of the wall of the tubular organ with the outer surface of the device may be utilized to determine the degree the device is collapsing the tubular organ. This may be desirable, for example, to control the degree of suction or drawing force to prevent damage or excess deformation of the tubular organ.

In a further aspect of the invention, an output of the at least one temperature sensor may generate a control input for a thermal ablation device. The input may be used to decrease the power output of the thermal ablation device in response to sensed increases in temperature. Other control methods may include having a visual readout of the temperature reading so that the operator can change the power output of the thermal ablation device based on the temperature reading, or so that the operator can be alerted of the rising temperature.

In another aspect of the invention, the device may be used to apply suction or other drawing action to the inside of a tubular organ to cause the tubular organ to contract, deform or otherwise decrease in, for example, size, diameter or caliber. In some embodiments, the device may be utilized to draw the esophagus wall inward, such as to move the esophagus or portion thereof away from another structure, such as away from portions of the heart. This may be desirable as treatments or therapies on the heart, such as, for example, cardiac ablation procedures, may cause damage to adjacent structures, such as the esophagus. Use of the device on the esophagus in areas adjacent to an area undergoing treatment may aid in spacing the esophagus away from the treatment area to protect it from or at least decrease incidental damage. In general, the application of suction to draw in and collapse the esophagus away from the treatment area may result in an atraumatic deformation without application of more traumatic forms of force to cause the deformation. Suction may minimize traction (stretch) on the esophagus both internally and externally due to the fibrous attachments of the esophagus to other structures in the chest. In turn, this diminishes the risk of perforating the esophagus. In some embodiments, the device may also employ sensors, such as discussed above, to monitor the location where temperatures are increased during a treatment to control the location and degree of suction or other drawing force being applied to the esophagus. The sensors may also, for example, act in a feedback control mechanism on the suction or other drawing force, or, for further example, in controlling or influencing the degree of temperature change being induced in the adjacent therapy.

In some embodiments, the device may include mechanical aids or struts for selectively moving the tubular organ, such as by deforming portions of the wall of the tubular organ upon applying suction. For example, one side of the tubular organ may be supported, such as with mechanically deploying struts or similar structures on the tube portion so as to limit the collapse of the tubular organ in a certain direction that would otherwise be caused by suction provided through the fenestrations. For further example, the struts may modify the collapsed shape of the tubular organ in conjunction with suction in order to create a narrow profile, for example relative to the pulmonary veins. The struts may not stretch the esophagus beyond its normal width, but instead maintain the normal width in one dimension while allowing the collapse to occur, shrinking the width in another dimension. As such, the struts may support the wall against collapse in a certain direction.

The present invention together with the above and other advantages may best be understood from the following detailed description of the embodiments of the invention and as illustrated in the drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE FIGURES

The drawings accompanying and forming part of this specification are included to depict certain aspects of the invention. A clearer impression of the invention, and of the components and operation of systems provided with the invention, will become more readily apparent by referring to the exemplary, and therefore non-limiting, embodiments illustrated in the drawings, wherein identical reference numerals designate the same components. Note that the features illustrated in the drawings are not necessarily drawn to scale.

DETAILED DESCRIPTION OF THE INVENTION

The detailed description set forth below is intended as a description of the presently exemplified methods, devices and systems provided in accordance with aspects of the present invention, and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and systems similar or equivalent to those described herein can be used in the practice or testing of the invention, the exemplified methods, devices and systems are now described.

The invention relates to devices and methods for collapsing a tubular organ, such as the esophagus, particularly to collapsing the tubular organ by inserting a device into the tubular organ and more particularly to collapsing the tubular organ by at least partially sealing off a section and moving the wall of the tubular organ, such as by application of suction. This invention further relates to methods of using such devices to move portions of a tubular organ away from an area undergoing a treatment or therapy, such as to minimize damage to the tubular organ. In general, a tubular organ may be in, without limitation, a human subject or other mammalian subject, as appropriate.

Figure 1:
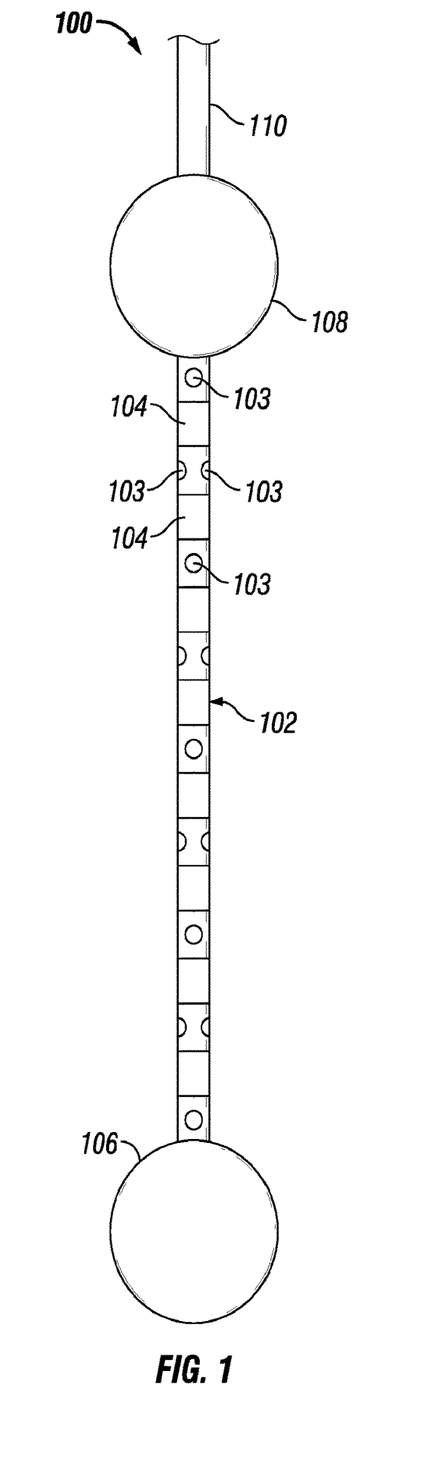
FIGS. 1 and 1a illustrate the external features of a device for collapsing a tubular organ.
Figure 1A:
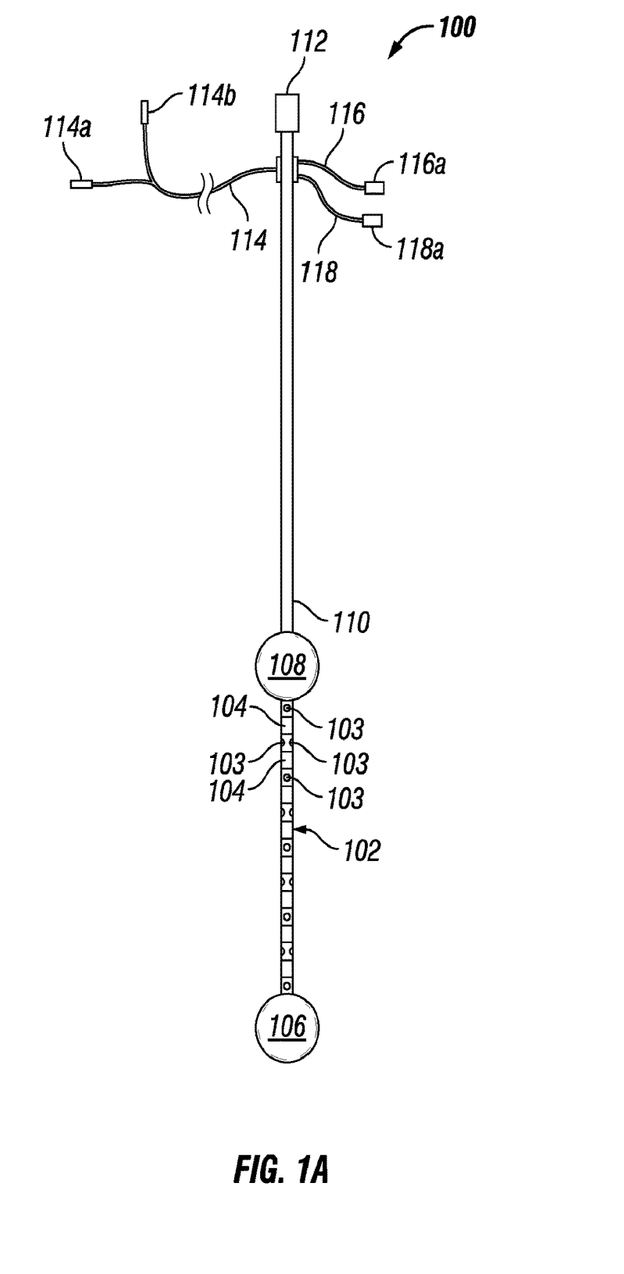

In general, a device for collapsing a tubular organ may be utilized on a variety of body structures, such as, for example, the esophagus. The device may generally include a tube which is inserted into a tubular organ proximal to an area to be affected by the device. FIGS. 1 and 1a illustrate an embodiment of a device 100 for collapsing a tubular organ including a tube portion 102 which is inserted into a tubular organ. To permit insertion of the device 100 into a tubular organ of a mammalian subject, the device 100 may have a narrow profile, smooth surfaces suitable to lubrication, and may be made of flexible materials to avoid perforating the esophagus. The materials used for the inserted portions of the device 100, such as the portions on and disposed adjacent to the tube portion 102, may generally be selected to be non-toxic, biocompatible or otherwise safe for internal use in the body.

In one aspect of the invention, the device may include a tube portion with at least one fenestration or other port through which suction or other means of drawing fluid or gas may be applied to the area surrounding the tube portion. In some embodiments, the tube portion may include a plurality of fenestrations or ports which may be utilized to apply suction or other means to different locations along the tube portion or, for example, to equalize the applied suction or other means along a larger area of the tube than with a single fenestration or port, as illustrated with fenestrations 103 in tube portion 102 of the device 100 in FIGS. 1 and 1a. The fenestrations or ports may be connected to an external source of suction or other means, such as through internal lumens formed into the tube portion or with internal tubes or conduits carried within the connecting conduit, as illustrated with the external connection 112 at the end of connecting conduit 110 that connects to the fenestrations 103.

The fenestrations or ports may take any appropriate form or number along the tube portion 102. In general, it may be desirable that the size and shape are appropriate to apply suction without clogging or causing incidental damage by drawing in significant amounts of tissue from the wall of the tubular organ. For example, when used for the esophagus, some embodiments may utilize circular or ellipsoidal fenestrations of less than about 0.5 cm in diameter. For further example, the length of the tube portion 102 with the fenestrations may be on the order of about 8 or 8.5 cm, such as to, for example, accommodate an appropriate length of esophagus.

Figures 4, 4A:
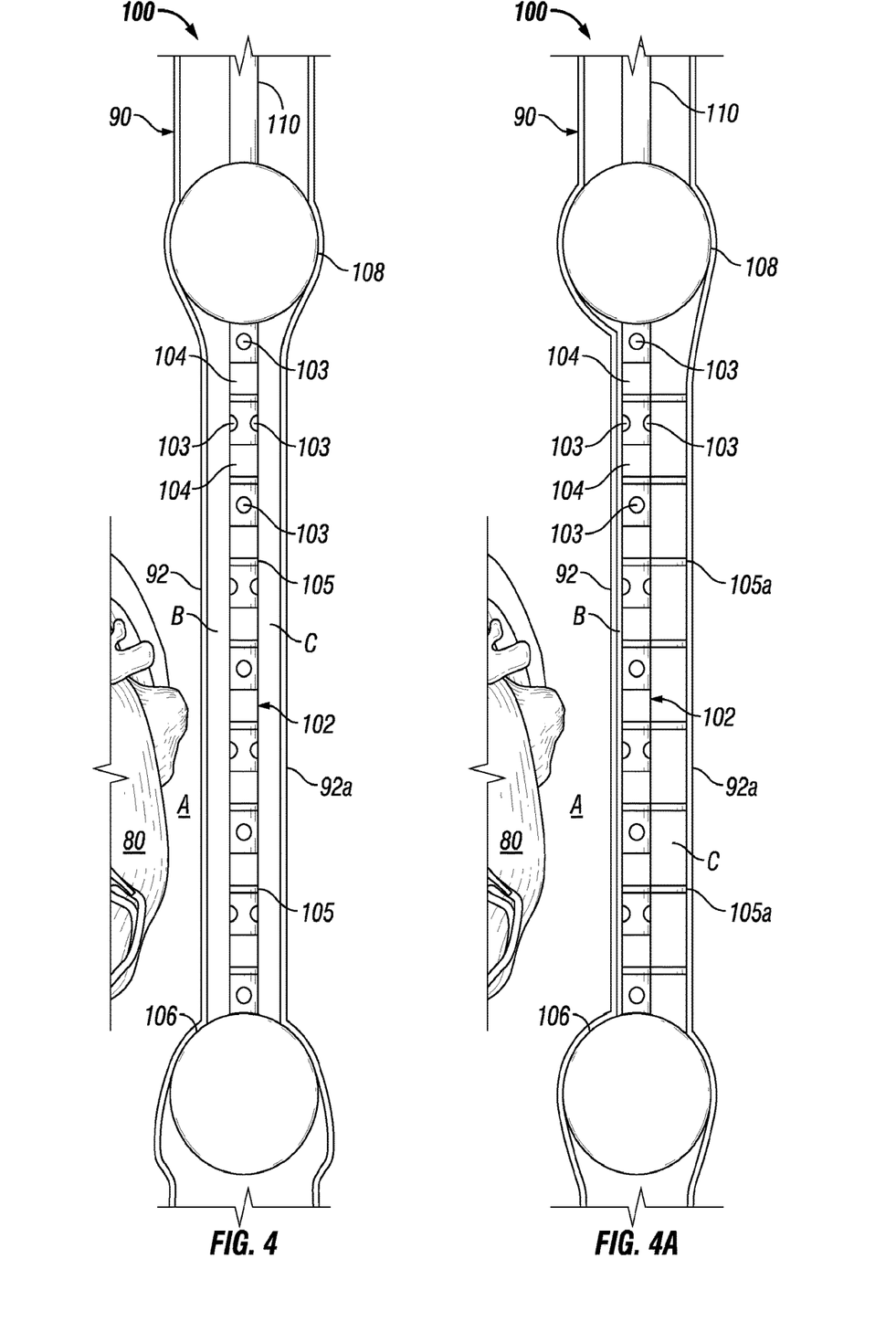
FIGS. 4 and 4a illustrate a device for collapsing a tubular organ with mechanically deploying struts.

In some embodiments, the device 100 may also include mechanical aids or struts for selectively moving the tubular organ. The struts may deform the cross sectional shape of the esophagus resulting from applying suction, such as by supporting portions of the wall of the tubular organ. For example, one side of the tubular organ may be supported, such as with mechanically deploying struts or similar structures on the tube portion 102, so as to limit the collapse of the tubular organ in a certain direction that would otherwise be caused by suction provided through the fenestrations 103. FIGS. 4 and 4a illustrate the device 100 with mechanically deploying struts 105 (retracted), 105a (deployed) while inserted into a tubular organ 90, such as an esophagus.

In another aspect of the invention, the device may further include at least one sealing feature to isolate a portion of the tubular organ to be affected by the device. FIGS. 1 and 1a illustrate a device 100 with at least two sealing features, shown with sealing balloons 106, 108. In general, the sealing feature may form at least a partial seal against the wall of the tubular organ. Sealing features may include, for example, deformable or compressible formations about the tube of the device. In some embodiments, the sealing feature may include a balloon or other feature that may be selectively expanded to contact the wall of the tubular organ or deflated/contracted to draw away from the wall, such as to aid in moving the device in the tubular organ without additional contact or friction with the wall. The balloon or other feature may also generally be connected to a fluid or gas source or withdrawing device, such as a suction line or pump, and the connection may generally be carried by lumen(s) or conduit(s)/tube(s) within the tube and connected to an external source or device, as illustrated with the inflation/deflation ports 116, 118 that connect through the connecting conduit 110 to the sealing balloons 106, 108, respectively. The ports 116, 118 may then be connected to, for example, a syringe, pump or other inflation/deflation device. The ports 116, 118 may further include locks or other mechanisms to maintain the level of inflation or deflation in the sealing balloons 106, 108, such as with locking valves 116a, 118a. Other selective sealing features may also be utilized, such as mechanically deploying struts, expanding stents, flattening/widening seals and/or any other appropriate feature or combination thereof.

In some embodiments, the device may include at least two sealing features along the length of the tube, such as, for example, that the fenestrations or ports (or groupings of them) lie between the two sealing features. The two sealing features may then, for example, seal off a particular length of the tubular organ at either end of the particular length to be deformed by the device. In other embodiments, three or more sealing features may be utilized to, for example, create multiple separate particular lengths to be deformed separately. Where balloons or other selectively expandable/contractible feature is utilized, they may be individually controlled or controlled in groups.

In a further aspect of the invention, the device may further include sensors or other features for aiding in locating the device within the tubular organ and/or for detecting a desired area of the tubular organ to be affected by the device. FIGS. 1 and 1a illustrate a plurality of sensors 104 disposed along the length of the tube portion 102. In some embodiments, desired areas of the tubular organ may be determined by detected conditions in the area, such as temperature, pressure, electrical resistance/conductivity, and/or any other appropriate condition or combination thereof. For example, temperature may be detected to determine where a tubular organ may need to be acted on, such as, for example, to aid in protecting it from damage from a temperature increase in the vicinity. This may utilize, for example, thermocouples, thermistors or other forms of temperature sensors as the sensors 104. The sensors 104 may also include, for example, location tracking features such as magnetic resonance imaging (MRI) or computed tomography (CT) fiducial markers, Hall Effect magnetic sensors or other appropriate location tracking features. For further example, pressure or other indicators of contact of the wall of the tubular organ with the tube of the device may be utilized to determine the degree the device is collapsing the tubular organ. This may be desirable, for example, to control the degree of suction or drawing force to prevent damage or excess deformation of the tubular organ. Sensors 104, for example, could detect the pressure of the wall of the tubular organ acting on the outside of the tube portion 102. The sealing features may also feature detection features for determining the level or state of deployment of the seal, such as a pressure sensor for use with inflating balloons.

As illustrated in FIGS. 1 and 1a, the sensors 104 may be connected to at least one external device, such as through sensor connection 114 that emerges from the connecting conduit 110 from a connection to the sensors 104 in the tube portion 102. For example, the sensor connection 114 may be utilized to monitor the temperature or other sensor feedback, such as through connection 114a, and/or provide feedback control signals through connection 114b.

Figure 2:
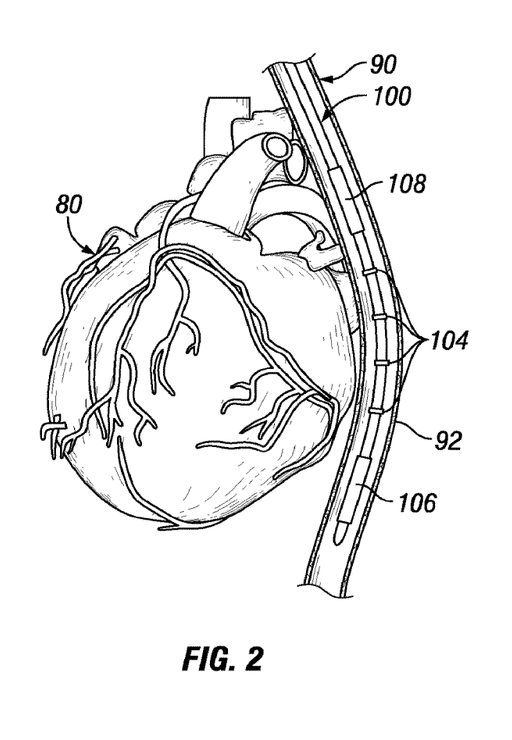
FIGS. 2, 2a and 2b illustrate use of a device to affect a portion of the esophagus near the heart.
Figure 2A:
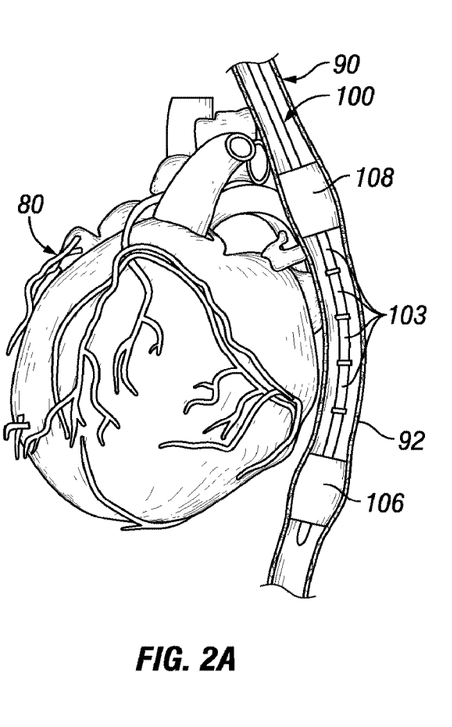
Figure 2B:
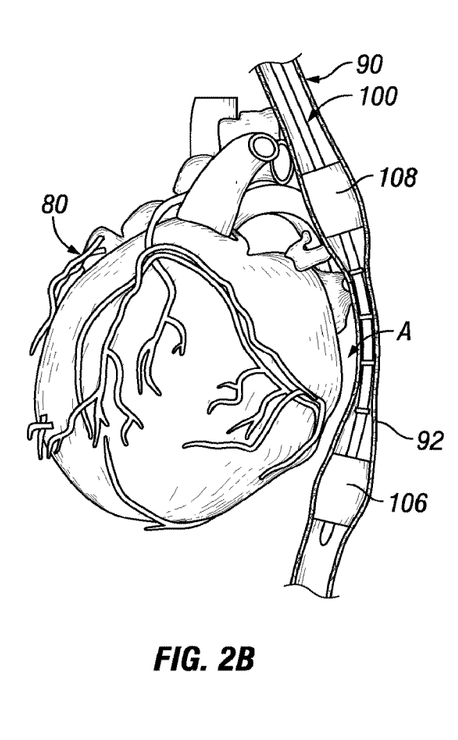

In another aspect of the invention, the device may be used to apply suction or other drawing action to the inside of a tubular organ to cause the tubular organ to contract, deform or otherwise decrease in, for example, size, diameter or caliber. FIGS. 2, 2a and 2b illustrate the use of the device 100 in the esophagus in relation to the heart. In some embodiments, the device may be utilized to draw the esophagus wall inward, such as to move the esophagus or portion thereof away from another structure, such as away from portions of the heart. FIG. 2 illustrates the tube portion 102 of the device 100 inserted into the esophagus 90 in an area adjacent to the heart 80. This may be desirable as treatments or therapies on the heart, such as, for example, cardiac ablation procedures, may cause damage to adjacent structures, such as the esophagus. Use of the device on the esophagus in areas adjacent to an area undergoing treatment may aid in spacing the esophagus away from the treatment area to protect it from or at least decrease incidental damage. In general, the application of suction to draw in and collapse the esophagus away from the treatment area may result in an atraumatic deformation without application of more traumatic forms of force. Deflection, such as accomplished mechanically by endoscopic catheter, for example, may cause trauma such as to the lumen of the esophagus, which may increase other forms of damage and susceptibility to complications. Such procedures may also generally require a greater deal of skill and care on the part of the practitioner which further complicates treatment.

As illustrated in FIG. 2, a portion of the heart 80 may be undergoing a thermal ablation treatment, such as to treat atrial fibrillation in an area of the heart 80 near the esophagus 90 using, for example, radio frequency (RF) ablation. A possible complication of this procedure is atrioesophageal fistula (AEF), in which heat related damage to the esophagus immediately adjacent to a pulmonary vein target site creates a communication between the atria and esophagus, which may be exacerbated by damage to the lumen of the esophagus by traumatic methods, as described above. Incidence of AEF after AF ablation is reported in the range of 0.1% to 0.25% and leads to a very high 80% mortality rate when observed. Prevention of this complication involves monitoring of esophageal temperatures.

As illustrated in FIG. 2, in some embodiments, the device may also employ sensors, such as discussed above, to monitor the location where temperatures are increased during a treatment to control the location and degree of suction or other drawing force being applied to the esophagus, as shown with thermocouples 104 on the tube portion 102 in the portion 92 of the esophagus 90 adjacent to the heart 80. The sensors may also, for example, act in a feedback control mechanism on the suction or other drawing force, or, for further example, in controlling or influencing the degree of temperature change being induced in the adjacent therapy, such as through the connections 114a, 114b, as discussed above in regards to FIG. 1a.

During the course of a treatment on the heart 80, the sealing features 106, 108 may be deployed, either preemptively or in response to a change, such as a change in temperature detected by the thermocouples 104, as illustrated with the deployed sealing balloons 106, 108 from FIG. 2 to FIG. 2a. In response to a temperature change detected, suction may then be applied between the sealing balloons 106, 108 through the fenestrations 103, which may lead to evacuation of gas and/or fluid in the esophagus 90 (which is typically present as air and/or secretions of the esophagus), and cause constriction of the portion 92 of the esophagus 90 to cause it draw away from the heart 80, as shown with the gap A forming in FIG. 2b. This gap A may be maintained for an appropriate duration, such as by locking the suction/vacuum level in the portion 92. This may be done, for example, by closing valves in the external connection 112 shown in FIG. 1a, or other device, such as a luer lock in the suction source. Without being bound to any particular theory, this may generally result in additional separation of the esophagus 90 from the area of the heart 80 being treated with minimal trauma to the esophagus 90, such as to the lumen, and with no special clinical expertise generally required to operate the device 100, as opposed to more intensive methods such as endoscopic deflection.

In some embodiments, struts or other mechanical features may also be utilized to aid in moving the esophagus. FIGS. 4 and 4a illustrate the device 100 inserted into an esophagus 90, with the portion 92 being the side wall facing the heart 80, and portion 92a being the side wall facing away, with the internal gaps between the device 100 and the wall B, C, respectively. While the struts 105 are not deployed and retracted, as shown in FIG. 4, the gaps B, C may be substantially even or similar in size, with the esophagus 90 being largely concentric with the device 100. The struts 105 may then be deployed to their extended state 105a, as illustrated in FIG. 4a, on one side, such as the side facing away from the heart 80 to support the portion 92a and prevent its collapse upon applying suction. The struts 105 may generally support the entire esophagus 90 to one side, shrinking the gap B and increasing the gap C, which may generally increase the gap A between the esophagus portion 92 and the heart 80. As such, the struts 105 deform the collapsed shape of the esophagus.

Figure 5:
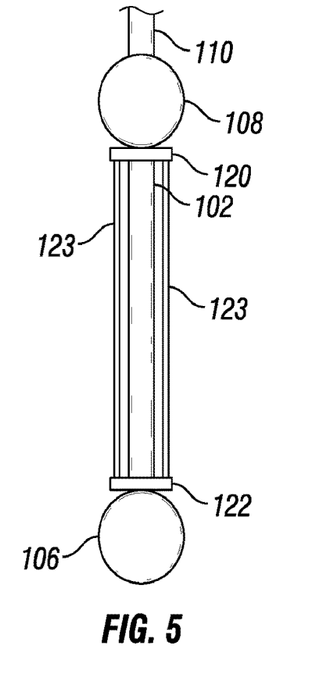
FIG. 5 illustrates a device for collapsing a tubular organ with longitudinal struts in the undeployed configuration.
Figure 5A:
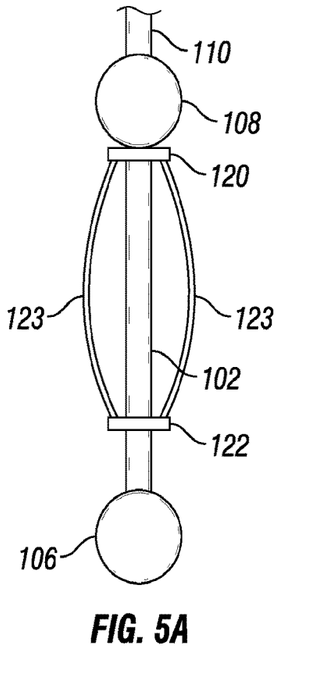
FIG. 5a illustrates the device shown in FIG. 5 with the struts deployed by moving a strut support toward a proximal end of the device.

In some other embodiments, struts may be longitudinally mounted along the tube portion of the device. FIGS. 5 and 5a illustrate the device 100 with struts 123 mounted along the tube portion 102 on proximal support 120 and distal support 122. As illustrated in FIG. 5, the struts 123 may be generally parallel to the tube portion 102 in their undeployed configuration. The struts 123 may then be deployed by decreasing the distance between the proximal and distal supports 120, 122, such as by pulling distal support 122 toward the proximal support 120, as shown in FIG. 5a, which may then cause the struts 123 to compress and/or bow outward. This may be utilized to deform the walls of a tubular organ, such as the esophagus, in order to cause the tubular organ to expand in one dimension and contract in another (i.e. flattening out). This may generally be done such that the expanding dimension is orthogonal to the direction of the desired increase gap between the tubular organ and the potential source of damage, such as the heart during a thermal ablation procedure.

Example of Esophagus Contraction Using a Suction Probe

Figure 3A:
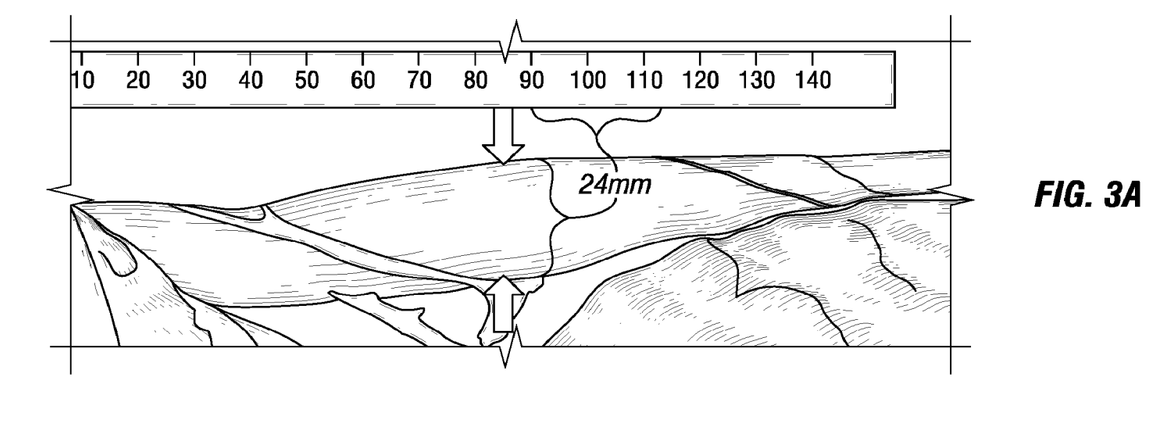
FIGS. 3a and 3b show an example of a device collapsing a portion of a porcine esophagus.
Figure 3B:
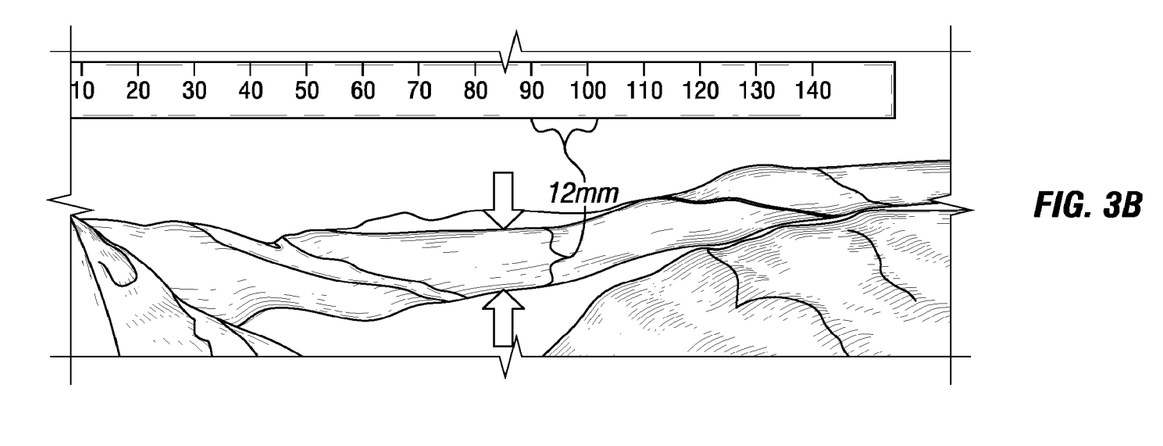

A device as described above was utilized consisting of an 18 French dual lumen tube with two occlusion balloons mounted 8 cm apart at the distal end of the tube. The occlusion balloons were mounted on the proximal and distal ends of an array of four thermocouples. Also between the occlusion balloons and around the thermistors are a series of suction ports (fenestrations). The thermocouples were terminated with connectors at the proximal end of the device, and interfaced with a hand held temperature monitor. Inflation and deflation of each occlusion balloon were independently maintained through separate lumens, while a separate suction port was provided through a third lumen connected to the fenestrations. The device was placed through the oropharynx into the esophagus with the distal end passed until the 8cm tube portion with suction ports and thermocouples lies posterior to the left atrium in example porcine specimens, including both excised and cadaveric. The occlusion balloons were inflated, and the esophagus was deformed through suction, with temperature detection to within 0.1° C. performed on a continuous basis. Devices were positioned at the appropriate level of the esophagus and activated to determine changes in diameter. FIG. 3a shows an example native esophagus after placement of the device with measured diameter of 24 mm. After inflation of balloons and activation of suction, the diameter of the esophagus decreased significantly to 12 mm, which was close to the approximate diameter of the device, as shown in FIG. 3b.

Example of Esophagus Contraction Using Struts on a Probe

Figure 5B:
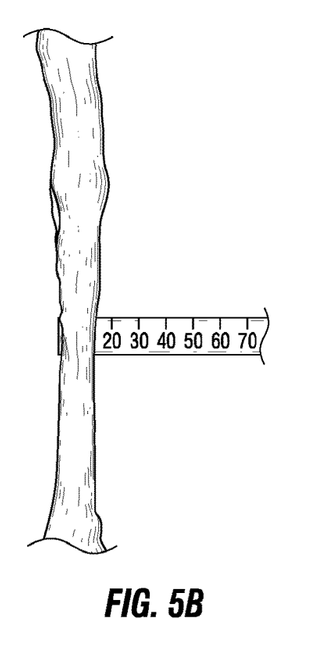
FIG. 5b shows a view of a device with longitudinal struts deployed in a porcine esophagus.
Figure 5C:
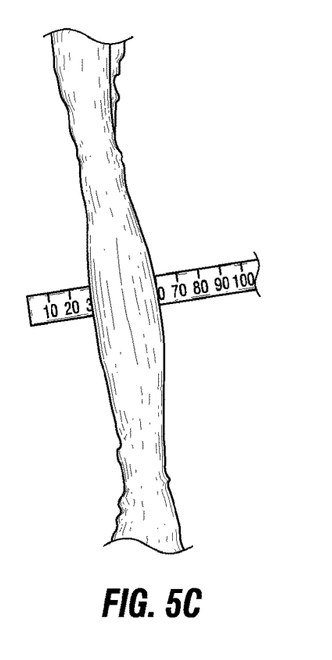
FIG. 5c shows another view of the device deployed in the porcine esophagus.

A device as depicted in FIGS. 5 and 5a was inserted into a porcine esophagus and the struts 123 were deployed as in FIG. 5a. FIGS. 5b and 5c illustrate the effects on the porcine esophagus. FIG. 5b shows the narrowest dimension, which is perpendicular to the direction of the deployment of the struts 123, and FIG. 5c shows the widest dimension, illustrating the flattening of the esophagus from the deployment of the struts.

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein, the meaning of "in" includes "in" and "on" unless the context clearly dictates otherwise.

What is claimed is:

1. A method for collapsing a tubular organ away from an area of an internal organ undergoing a treatment by a thermal ablation device to minimize thermal damage to the tubular organ, the method comprising:
   inserting a device into a portion of a tubular organ of a mammalian subject, said device comprising:
      a tube portion having an outer surface and at least one internal lumen, wherein said at least one internal lumen connects to a plurality of fenestrations, the plurality of fenestrations being disposed on said outer surface of said tube portion;
      a connecting conduit coupled to a proximal end of said tube portion, said connecting conduit housing a suction line connected to said at least one internal lumen and interfacing with a suction source;
      a first sealing feature disposed at said proximal end of said tube portion; and
      a second sealing feature disposed at a distal end of said tube portion;
      wherein said outer surface of said tube portion extends from said proximal end to said distal end and is completely sealed except at said plurality of fenestrations,
   forming a sealed area of said portion of said tubular organ by expanding said first and second sealing features against a wall of said tubular organ; and
   applying suction at said plurality of fenestrations by activating said suction source;
   evacuating gas or fluid in a volume enclosed by said outer surface, said first sealing feature, said second sealing feature, and said sealed surface, wherein the gas or fluid is evacuated through said plurality of fenestrations;
   drawing said wall at said sealed area toward said tube portion;
   decreasing outer dimensions of said sealed area of said tubular organ; and
   performing the treatment of the area of an internal organ by the thermal ablation device while the outer dimensions of said sealed area of said tubular organ are decreased.

2. A system for treating an internal organ comprising:
   a thermal ablation device for treating an internal organ, said thermal ablation device being adapted to receive control input;
   a device for collapsing a tubular organ away from an area of said internal organ undergoing a treatment by the thermal ablation device to minimize thermal damage to the tubular organ, said device being configured for insertion into said tubular organ, said device comprising:
      a tube portion having an outer surface and at least one internal lumen, wherein said at least one internal lumen connects to a plurality of fenestrations, the plurality of fenestrations being disposed on said outer surface of said tube portion;
      a connecting conduit coupled to said tube portion, said connecting conduit housing a suction line connected to said at least one internal lumen and interfacing with a suction source;
      first and second sealing features disposed at proximal and distal ends of said tube portion, respectively, said first and second sealing features being capable of forming reversible seals against a wall of said tubular organ, wherein said first and second sealing features are configured to selectively expand to contact the wall of the tubular organ and contract to draw away from the wall, and wherein said outer surface of said tube portion extends from said proximal end to said distal end and is completely sealed except at said plurality of fenestrations; and
      at least one temperature sensor disposed on said tube portion and having an output;
   wherein said output of said at least one temperature sensor generates a control input for said thermal ablation device by decreasing a power output of said thermal ablation device in response to sensed increases in temperature.

3. The method or system of claim 1 or 2, wherein said first and second sealing features each comprise a sealing balloon attached to at least one inflation/deflation device through said connecting conduit.

4. The method or system of claim 1 or 2, wherein said plurality of fenestrations are disposed at regular intervals on said outer surface of said tube portion.

5. The method of claim 1, wherein at least one sensor is disposed on said tube portion, said at least one sensor being selected from the group consisting of a temperature sensor, a pressure sensor, an electrical conductivity/resistance sensor, a position sensor, an MRI fiducial marker and a CT fiducial marker.

6. The method of claim 1, wherein at least one temperature sensor is disposed on said tube portion, said at least one temperature sensor having an output that controls a power output of the thermal ablation device.

7. The method or system of claim 1 or 2, wherein said tube portion has a length of about 8 centimeters.

8. The method or system of claim 1 or 2, wherein said first and second sealing features form seals with a diameter of about 3 centimeters.

9. The method or system of claim 1 or 2, wherein each of said plurality of fenestrations is smaller than about 0.5 centimeters in diameter.

10. The method or system of claim 1 or 2, wherein struts are adapted to deploy outward from said tube portion.

11. The method or system of claim 1 or 2, wherein said tubular organ comprises an esophagus.

12. The system of claim 2, wherein said thermal ablation device comprises an RF ablation device for treating atrial fibrillation in a heart.

13. The method of claim 1, wherein said decreasing the outer dimensions of said sealed area of said tubular organ comprises shrinking in diameter of about 50%.

14. The method of claim 1 further comprising supporting a portion of said wall against drawing of said wall using deployable struts.

15. The method or system of claim 1 or 2, wherein the tube portion does not include a deflection catheter.

16. The method or system of claim 1 or 2, wherein said internal organ is a heart.

* * * * *